(12) United States Patent
Howlett et al.

(10) Patent No.: US 6,997,910 B2
(45) Date of Patent: Feb. 14, 2006

(54) MULTI-CHAMBER, SEQUENTIAL DOSE DISPENSING SYRINGE

(75) Inventors: Michael Wallace Howlett, Salt Lake City, UT (US); James Victor Mercer, West Jordan, UT (US); Gale H. Thorne, Jr., Bountiful, UT (US); Gale H. Thorne, Bountiful, UT (US)

(73) Assignee: Infusive Technologies, LLC, Bountiful, UT (US)

( * ) Notice: Subject to any disclaimer, the term of this patent is extended or adjusted under 35 U.S.C. 154(b) by 94 days.

(21) Appl. No.: 10/838,101

(22) Filed: May 3, 2004

(65) Prior Publication Data

US 2005/0245880 A1 Nov. 3, 2005

(51) Int. Cl.
*A61M 5/00* (2006.01)
*A61M 5/315* (2006.01)

(52) U.S. Cl. ...................................... 604/191; 604/231
(58) Field of Classification Search ................ 604/191, 604/218, 89–91, 184, 213, 226, 231, 237, 604/238
See application file for complete search history.

(56) References Cited

U.S. PATENT DOCUMENTS

| | | | |
|---|---|---|---|
| 3,976,068 A | | 8/1976 | Lundquist |
| 4,643,721 A | * | 2/1987 | Brunet ........................ 604/191 |
| 4,668,223 A | | 5/1987 | Grotenhuis |
| 4,792,329 A | | 12/1988 | Schreuder |
| 4,929,230 A | | 5/1990 | Pfleger et al. |
| 5,171,220 A | | 12/1992 | Morimoto |
| 5,236,420 A | | 8/1993 | Pfleger et al. |
| 5,298,024 A | * | 3/1994 | Richmond .................... 604/90 |
| 5,695,465 A | | 12/1997 | Zhu |
| 5,704,918 A | * | 1/1998 | Higashikawa ............... 604/191 |
| 5,713,857 A | | 2/1998 | Gremard et al. |
| 5,743,886 A | | 4/1998 | Lynn et al. |
| 5,743,890 A | | 4/1998 | Hjertman et al. |
| 5,785,682 A | * | 7/1998 | Grabenkort .................. 604/82 |

(Continued)

OTHER PUBLICATIONS

"Debioject (ClipnJect)" from www.debiotech.com, pp. 1-3.*

(Continued)

*Primary Examiner*—Sharon Kennedy
(74) *Attorney, Agent, or Firm*—Gale H. Thorne, Patent Agent

(57) ABSTRACT

A valve assembly is disclosed which effectively partitions a syringe into proximal and distal chambers to provide a multi-chamber, sequentially dispensing syringe apparatus. The valve assembly may be effectively used with a variety of standard, currently available commercial syringes and pre-filled syringes. Incorporated in the valve assembly is a valved stopper having a valve (which may be a slit valve), an impact sensor which opens the valve upon impact between the valve assembly and internal distal end of the syringe and a gas separator which separates liquid from gas disposed in the proximal chamber to assure gas is not delivered therefrom. The valve assembly is displaced as a plunger of the syringe is displaced via communication through fluid in the proximal chamber of the syringe. The actuator has a latching feature which latches the valve to an open state after being opened by the impact sensor. The gas separator has a proximally disposed orifice which facilitates priming. The valve assembly may be made from two parts. One part, a valved stopper, may be molded from the same rubber based material used in syringe plunger stoppers. The second part, the valve actuator, may be injection molded as a single part. A synthetic resinous material which is compatible with manufacture of living hinges my be used for the second part. Multiple valve assemblies may be used in a single syringe barrel.

27 Claims, 10 Drawing Sheets

U.S. PATENT DOCUMENTS

| | | |
|---|---|---|
| 5,830,193 A | 11/1998 | Higashikawa |
| 5,851,200 A | 12/1998 | Higashikawa et al. |
| 5,899,881 A | 5/1999 | Grimard et al. |
| 6,027,481 A | 2/2000 | Barrelle et al. |
| 6,077,252 A | 6/2000 | Siegel |
| 6,120,478 A | 9/2000 | Moore et al. |
| 6,132,400 A | 10/2000 | Waldenburg |
| 6,142,977 A | 11/2000 | Kolberg et al. |
| 6,149,628 A * | 11/2000 | Szapiro et al. .............. 604/191 |
| 6,161,364 A | 12/2000 | Kolberg |
| 6,544,233 B1 | 4/2003 | Fukui et al. |
| 6,602,223 B1 | 8/2003 | Szapiro et al. |
| 6,622,721 B1 | 9/2003 | Vedrine et al. |
| 6,641,561 B1 | 11/2003 | Hill et al. |
| 6,723,074 B1 * | 4/2004 | Halseth ...................... 604/201 |
| 6,740,062 B1 * | 5/2004 | Hjertman .................... 604/187 |
| 6,866,653 B1 * | 3/2005 | Bae ............................ 604/191 |

OTHER PUBLICATIONS

Debiotech brochure from internet address www.debiotech.com (accessed May 25, 2004).

* cited by examiner

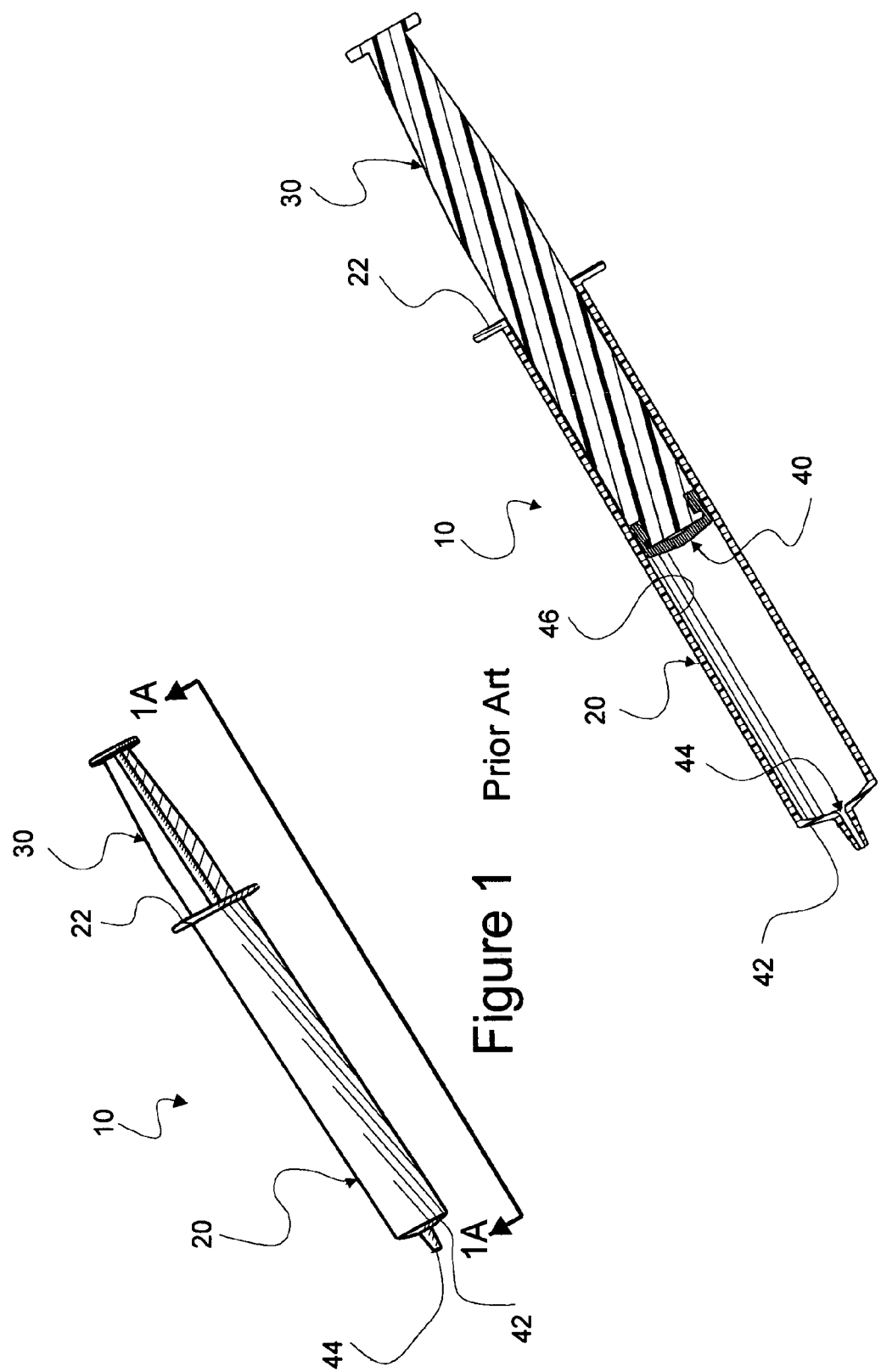

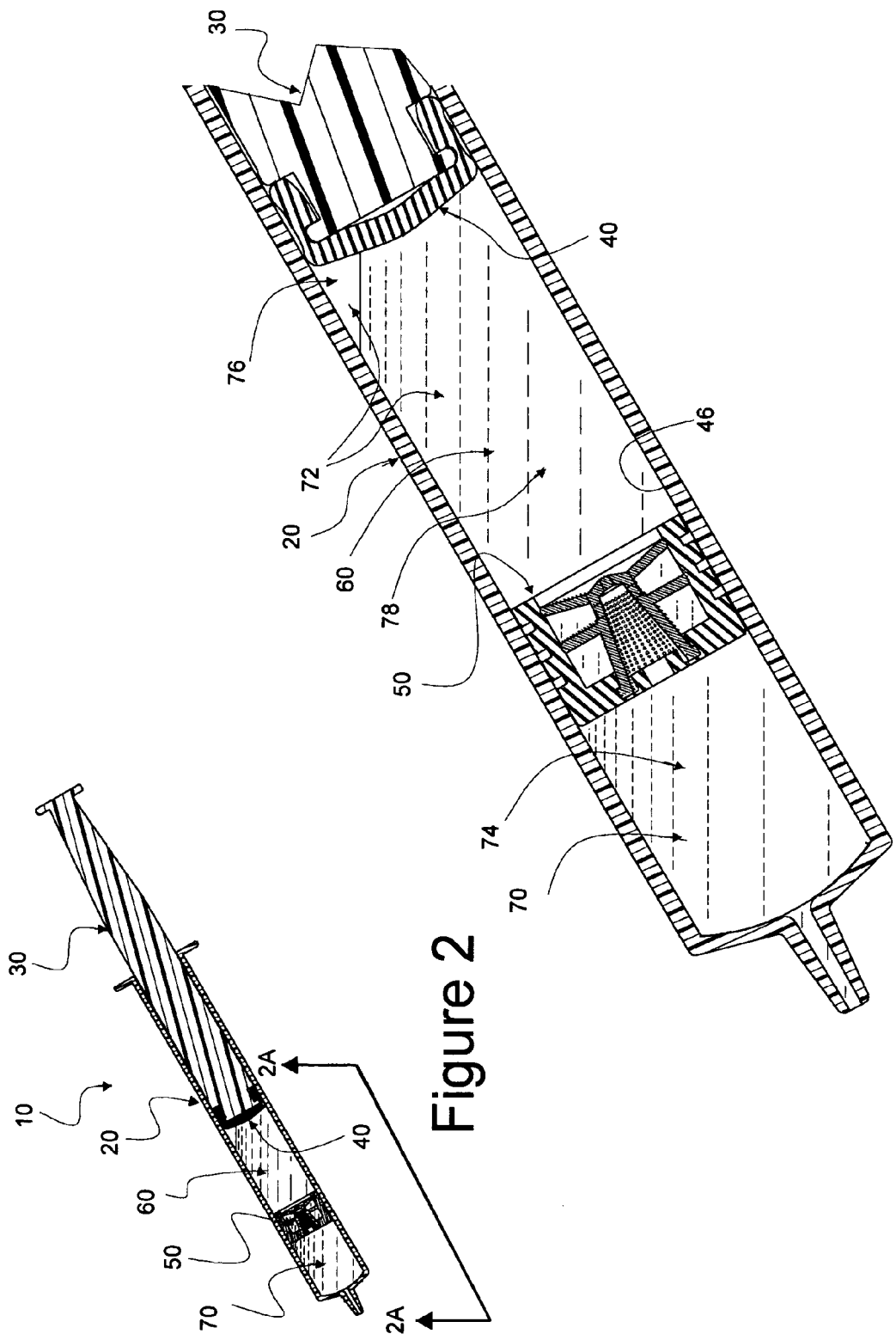

MULTI-CHAMBER, SEQUENTIAL DOSE DISPENSING SYRINGE

FIELD OF INVENTION

This invention relates to multi-chamber syringes and, in particular, to syringes which dispense fluid from each chamber sequentially.

DESCRIPTION OF RELATED ART

During the last forty years, parenteral drug delivery has become increasingly common and sophisticated. It is currently estimated that nearly 90% of hospital patients receive IV medications, often through a variety of apparatus, including expensive electronic IV pumps and multi-channel infusion systems. Home care patients may receive antibiotics through an elastomeric "ball" pump. Syringe pumps are common in many hospital and alternate site settings and are often used as a low cost alternative to more expensive IV pumps.

Virtually all IV medications must be flushed into the vascular system with saline or a similar compatible flushing fluid. Such flushing assures that the patient receive a full dose of medication, some of which otherwise might remain in an associated IV tubing or catheter. Flushing also assures that a subsequently infused incompatible medication does not come in contact with a previous one. It is well known in the infusion art that flush solutions are also used to keep an infusion line patent or open.

With rising healthcare costs, and an ever increasing shortage of nurses and pharmacists, streamlining basic procedures, such as IV catheter flushing can save significant clinician time. Noting that flushing usually necessitates use of a second flushing syringe (which is often currently factory filled), the flushing syringe represents added cost, not only in clinician time, but in terms of required additional syringes. Use of multiple syringes also increases risk of medication error (incorrect selection of flushing liquid) and introduction of microorganisms (a function of number of IV line or catheter accesses).

As an example, it is currently estimated that there are over 500 million antibiotic and chemotherapy medications administered annually in the United States. Each of these administrations require a follow-on flush, necessitating use of a second syringe. Combining antibiotic or chemotherapy and flush medications in one multi-chamber, sequential dose syringe promises to save on the order of one-half billion syringes and the additional time required for two syringe delivery yearly in the United States alone.

Multi-chamber syringes in various forms are well known. Commonly, multi-chamber syringes are offered for use as mixing syringes and for sequential delivery of disparate fluids, maintaining the fluids separate until delivered. Mixing syringes most often provide features for mixing contents of the chambers and for delivering the mixed fluids simultaneously. This invention is not related to mixing syringes.

Generally, within each serial delivery syringe, chambers are separated by an intermediate sliding stopper which receives motive force communicated through an intermediate fluid from a primary stopper which is part of a plunger assembly against which an external force is applied. For the disparate fluids to be dispensed sequentially or serially, each intermediate stopper must provide a fluid tight seal until all fluid from a distal chamber is evacuated from the syringe. Once the syringe is so purged, that intermediate stopper must be breached or bypassed to permit dispensing of the contents of a proximal or intermediate chamber.

An example of a multi-chamber syringe is provided in U.S. Pat. No. 4,929,230 titled SYRINGE CONSTRUCTION and issued May 29, 1990 to Frederick W. Pfleger (Pfleger). Pfleger teaches a distortable piston which is used as the intermediate stopper. The piston of Pfleger collapses upon contact with a distal end of a syringe to provide a fluid pathway to dispense contents from the intermediate chamber.

While a syringe made, as an example, according to Pfleger appears to provide a solution for sequentially dispensing disparate fluids, there are a series of concerns which would necessarily be associated with using such a syringe to dispense sequential doses of medications. A first concern arises, for example, when it is recognized that such a syringe may be used to dispense an accurately measured dose of a very expensive medication into an IV apparatus from a distal chamber of a multi-chamber syringe. Then, immediately following dispensing the first medication, a volume of a following solution is dispensed through the IV line to flush the first solution fully.

Clearly, a deformable piston, having a hollow center, such as the stopper of Pfleger would not have zero dead space. Also, it is well known that filling procedures for contents of the proximal chamber may permit a quantity of air (or other gas) to be trapped therein. It may be noted that even if such gas is not trapped during filling, free gas may be found in the proximal chamber simply as a result of out-gassing. Pfleger does not teach a way of purging the proximal chamber of gas, making such a system unacceptable for use in directly administering liquid medications to a patient. While other art may provide more effective ways to deal with the dead space issue, there is no known art which teaches a way of delivering only liquid from the proximal or intermediate chambers. That such may be a problem is recognized by U.S. Pat. No. 5,236,420 titled BYPASS, PRESSURIZED PISTON FOR CHAMBERS issued Aug. 17, 1993, also to Frederick W. Pfleger, discloses a valved plunger which may be used to evacuate gas from a proximal syringe chamber.

Other art, such as U.S. Pat. No. 6,027,481 issued Feb. 22, 2000 to Laurent Barrelle, et al. (Barrelle) and U.S. Pat. No. 5,851,200 issued Dec. 22, 1998 to Tetsure Higashikawa, et al. (Hagashikawa) disclose multi-chamber syringes with sliding valves. However, in each case Barrelle and Higashikawa teach special structure imposed upon a syringe barrel (a channel in the case of Barrelle and a bulge in the case of Higashikawa) which is used to provide a fluid pathway about a stopper.

Another U.S. Pat. No. 6,723,074 B1, titled SEQUENTIAL DELIVERY SYRINGE and issued Apr. 20, 2004 to Thor R. Halseth (Halseth) teaches a sequential delivery syringe which utilizes a modification to a discharge opening of a syringe for providing access to a rear chamber of a two chamber syringe. The modification comprises affixing a piercing member at the discharge opening. The piercing member punctures a "mid-piston" and a collapsible bag disposed in a rear chamber to provide access to fluid in the bag. Access occurs when the mid-piston is displaced by action of a plunger and stopper piston to cause the mid-piston and bag to contact the piercing member.

BRIEF SUMMARY AND OBJECTS OF THE INVENTION

In brief summary, this novel invention alleviates all known problems related to providing an effective multi-chamber, sequential dose dispensing syringe. Inherently, the invention involves a stopper assembly which operates within a standard, substantially constant diameter syringe barrel to separate a distal chamber from a proximal chamber. Before dispensing, the distal chamber contains a first volume of liquid. The proximal chamber contains a disparate second volume of fluid. A closed valve in the stopper assembly keeps the contents of each chamber separate from the other.

The stopper assembly comprises two elements, a valved stopper and a valve actuator. The valved stopper contains the valve mechanism. Action upon a plunger associated with the syringe communicates through the second volume of fluid to displace the stopper assembly thereby dispensing liquid from the distal chamber. Upon complete evacuation of the liquid from the distal chamber, the valve is opened by action of the valve actuator to permit sequential and selective dispensing of liquid contents from the proximal chamber.

In a preferred embodiment of the invention, the valve closure mechanism is a slit through the distal face of the valved stopper. It should be noted that a stopper assembly according to the instant invention operates in an unmodified standard syringe barrel, requiring no special barrel features. Examples of some previously cited special features which may be placed in modified syringe barrels are found in Barelle and Hagashikawa.

Selective opening of the valve is based upon a common geometry of all known, currently commercially available standard syringe barrels. All such syringe barrels have a substantially constant diameter hollow barrel abruptly closed at a distally disposed inner surface. Distally, the inner surface comprises an orifice through which fluid is dispensed from the barrel. Generally, a plunger with an associated stopper affixed thereto is provided for displacing fluid through the barrel and orifice.

To prevent premature mixing of the disparate solutions in the two chambers, the stopper assembly must open only upon being displaced to the most distal end of the syringe barrel. For this reason, the actuator comprises a member which detects collision between a surface of the distal wall of the valved stopper and the distal inner surface and reacts to open the valve. In addition, to assure that the valve remains absolutely closed until fluid is dispensed from the distal chamber, the detecting member is disposed to apply a closing force upon the valve until displaced by the collision.

To assure effective displacement of the detecting member to open the valve, the valve actuator must be displaced as the valved stopper is displaced. As is well understood in fluid mechanics, displacement of a substantially incompressible fluid in a proximal chamber of a syringe barrel interposed between a combination of a proximally disposed plunger and associated stopper and a distally disposed valve assembly, results in measured displacement of the valve assembly as the plunger and associated stopper are displaced. The valved stopper and valve actuator comprise an interlocking interface which causes the valve actuator to be displaced as the valved stopper is displaced.

Opening a slit valve can be accomplished by outward displacement of a portion of the valved stopper transverse to the split. To accomplish this, the valve actuator comprises a body part, which is securely affixed, via the interlocking interface, to the valved stopper and an associated collision detecting arm. The arm is hingedly affixed to the body part. Upon collision between the valved stopper and inner surface of the syringe barrel, the detecting arm articulates about the hinge to displace a portion of the valved stopper and, thereby, open the slit valve.

In one embodiment, an outwardly distending arm is rigidly affixed to the detecting arm to extend into to contact with a portion of the inner surface of the valved stopper. Before the collision, the distending arm is in compressive contact with the inner surface of the valved stopper, adding to the forces which act upon the slit to keep it closed. As the detecting arm is articulated, the outwardly distending arm is arcuately displaced proximally until compressive forces received from the inner surface of the valved stopper act to retain the slit valve in an open state. In this manner, once opened, the slit valve requires no additional force to stay open and operation of the plunger and associated stopper need no additional force to keep the valve open. Thus, a slit valve is maintained in a closed position until the valve assembly collides with the inner proximal surface of the end of the syringe barrel and is thereafter effectively opened to permit dispensing of fluid from the proximal chamber.

However, when prefilled doses are stored in the proximal chamber for ultimate use, it is not uncommon for gas (most commonly air) to collect in a non-significant bubble size there inside. It is not good medical practice to dispense that gas into a patient line (e.g. IV line). To preclude such an occurrence, the body comprises a gas separator. The gas separator is formed in a centrally disposed portion of the body and may be made as a hollow frustoconical shape, being open at the bottom. A series of very small, closely spaced holes are dispersed about the conical sides of the separator. The top of the frustoconical shape is closed except for a hole which is sufficiently large to permit purging gas from the separator. The open bottom of the separator (frustoconical shape) is disposed distally within the valved stopper into contact with the inner surface of the stopper about the slit. An outwardly projecting rim about the bottom of the separator provides an interlocking surface for a complimentary groove molded into the valved stopper about the slit.

Also, stability of a freely displaced valve assembly within the barrel of a syringe must be considered. The body of the actuator is provided with sufficient radially extending appendages to maintain the valved stopper in a stable state such that the plane of the slit is transverse to the plane of the barrel of the syringe throughout displacement of the valve assembly.

Of considerable importance is the opportunity to use more than one valve assembly in a syringe barrel. For example, if two valve assemblies are so used, a proximal, a distal and an intermediate chamber so created yields an opportunity to replace three syringes with one syringe.

The valve assembly may be made from only two parts. The valved stopper may be molded from flexible synthetic resinous material, consistent with material used in plunger stoppers. The valve actuator may be injection molded from semi rigid synthetic resinous material from which living hinges may be molded and which is appropriately inert and non-interactive with solutions stored in the proximal chamber. Such a material may be polypropylene.

In summary, the valve assembly:
 provides a selective partitioning between proximal and distal chambers of a multi-chamber syringe.
 may be used in standard (off the shelf) commercial syringes having constant diameter hollow barrels.
 provides a closed valve which is opened only upon collision between the valve assembly and inner surface of the distal end of the syringe.
 comprises an interlock which effectively latches the valve in an open state as liquid is dispensed from the proximal chamber.

separates gas from liquid and only dispenses liquid from the proximal chamber.

comprises parts which stabilize the valve assembly throughout displacement.

multiple valve assemblies may be used in a syringe barrel to provide effective substitution for more than two syringes.

Accordingly, it is a primary object to provide a valve assembly which partitions a standard commercial syringe to make a multi-chamber syringe.

It is a fundamental object to provide a valve assembly for a syringe which keeps two disparate fluids apart until one of the fluids has been dispensed.

It is an important object to provide a valve assembly which has a low dead space for liquid dispensed from a distal chamber.

It is another important object to provide a valve assembly having an operable slit valve.

It is yet another object to provide a valve actuator which senses collision between a valve assembly and an inner surface at the end of a syringe to force a valving slit open.

It is another primary object to provide a valve assembly which opens to dispense liquid from a proximal chamber only after liquid from a distal chamber has been dispensed.

It is a basic object to provide a valve assembly to separate gas from liquid in the proximal chamber such that only liquid is dispensed from the proximal chamber.

It is a very important object to provide a valve actuator which is a stabilizer for an associated valved stopper in a syringe barrel.

It is an object to provide an interlock which latches an opened valve to the open state.

It is an object to provide an interface between a valved stopper and a valve actuator such that displacement of the valved stopper likewise displaces the valve actuator.

It is an object to provide a valve assembly which may be used in plural numbers in a syringe.

These and other objects and features of the present invention will be apparent from the detailed description taken with reference to accompanying drawings.

BRIEF DESCRIPTION OF THE DRAWINGS

FIG. 1 is a perspective of an exemplary commercial syringe with a plunger and stopper assembly disposed within the barrel of the syringe (prior art).

FIG. 1A is a section of the syringe seen in FIG. 1 taken along lines 1A—1A (prior art).

FIG. 2 is a section of a syringe, similar to the section seen in FIG. 1A, but with a valve assembly distally disposed relative to a plunger and stopper similar to the plunger and stopper of the syringe of FIG. 1.

FIG. 2A is a magnified portion, taken along lines 2A—2A, of the syringe seen in FIG. 2.

DETAILED DESCRIPTION OF THE ILLUSTRATED EMBODIMENTS

Figure 15:
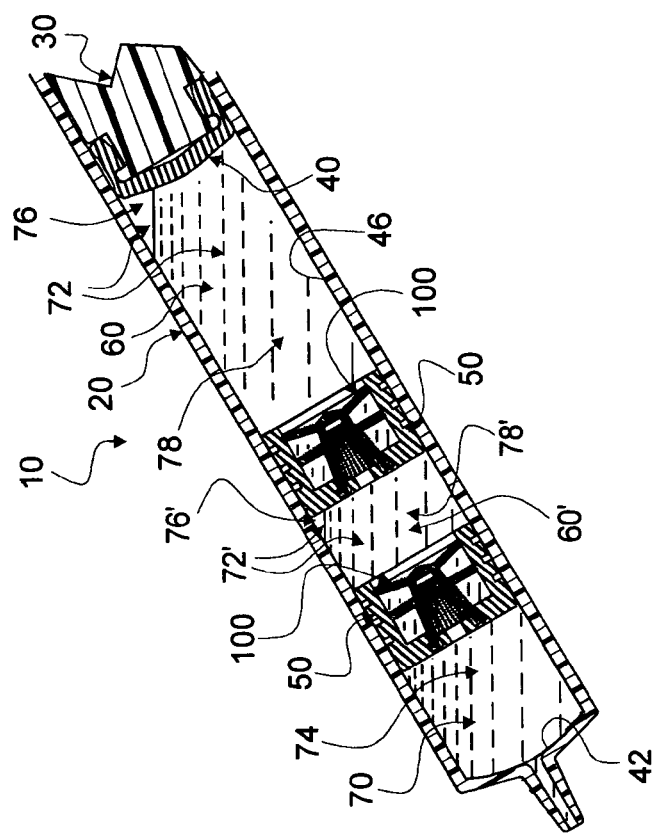
FIG. 15 is a section of a syringe, similar to the section seen in FIG. 2A, but with two valve assemblies distally disposed relative to a plunger and stopper similar to the plunger and stopper of the syringe of FIG. 1.

In this description, the term proximal is used to indicate the segment of a device normally closest to a clinician using the device. The term distal refers to the opposite end. Primes of numbers are used to represent parts which are similar, but not identical to other parts having the same numbers. Reference is now made to embodiments illustrated in FIGS. 1–15 wherein like numerals are used to designate like parts throughout.

As used herein, the term "fluid" is defined to be a substance (either liquid or gas) which tends to flow or to take the shape of its container. The term "gas" is defined to be a fluid that expands indefinitely and which may be understood in most circumstances within the scope of this document to be consistent with air. The term "liquid" is a substance which is free flowing like water, but which is neither solid nor gaseous.

Prior art syringes (as exemplified by syringe 10) in FIGS. 1 and 1A, are available from a large number of commercial companies worldwide. Such syringes typically comprise an elongated hollow syringe barrel 20 which is open at a proximal end 22 to receive a syringe plunger 30 and stopper 40 and closed at a distal end 42 about a fluid transmission orifice 44. Generally, barrel 20 is of substantially constant diameter (within tolerances allowed by manufacturing methods, such as by injection molding for barrels made from synthetic resinous materials). Stopper 40 is compressible and sufficiently elastic when compressed to provide an efficient wiping action along the length of an internal cylindrical surface 46 of barrel 20.

As seen in FIG. 2, a valve assembly 50 is inserted into barrel 20 to divide space within barrel 20 into a proximal chamber 60 and a distal chamber 70. As seen in FIGS. 2 and 2A, each chamber, 60 and 70, may be filled with a bolus of fluid, 72 and 74, respectively. It may be noted that, when chamber 60 is substantially filled with a bolus of fluid (which should be mostly an incompressible liquid), displacement of stopper 40 results in substantially the same displacement of valve assembly 50. It may also be noted that fluid 72 disposed in chamber 60 is trapped and may contain a small bubble of gas (likely air), numbered 76 associated with other liquid 78 also contained therein. Such gas 76 may be inadvertently trapped therein during filling or may be the result of outgassing or other gas producing phenomena following insertion of stopper 40 into barrel 20. In any event, such gas must be seriously considered and dealt with when such a device is used to dispense liquid to a patient to assure gas (air) is not injected into a patient line.

Figure 3:
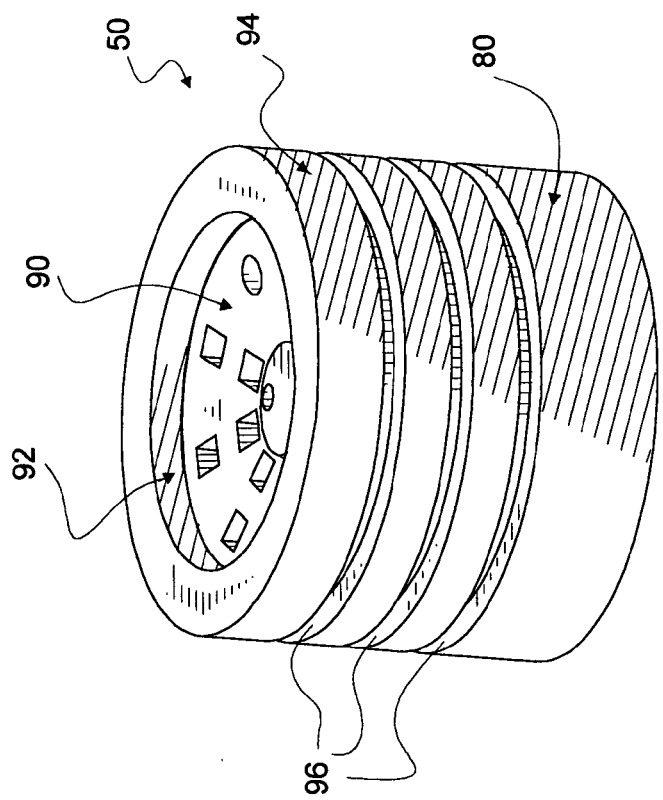
FIG. 3 is a perspective of the valve assembly seen in the syringe barrel in FIG. 2.

A valve assembly 50, apart from a barrel 20, is seen in FIG. 3. Although more parts may be used in a valve assembly made according to the instant invention, valve assembly 50 comprises just two parts, a valved stopper 80 and a valve actuator 90. Note that valved stopper 80 has a hollow cylindrical well 92 into which valve actuator 90 is displaced for use.

Figure 4:
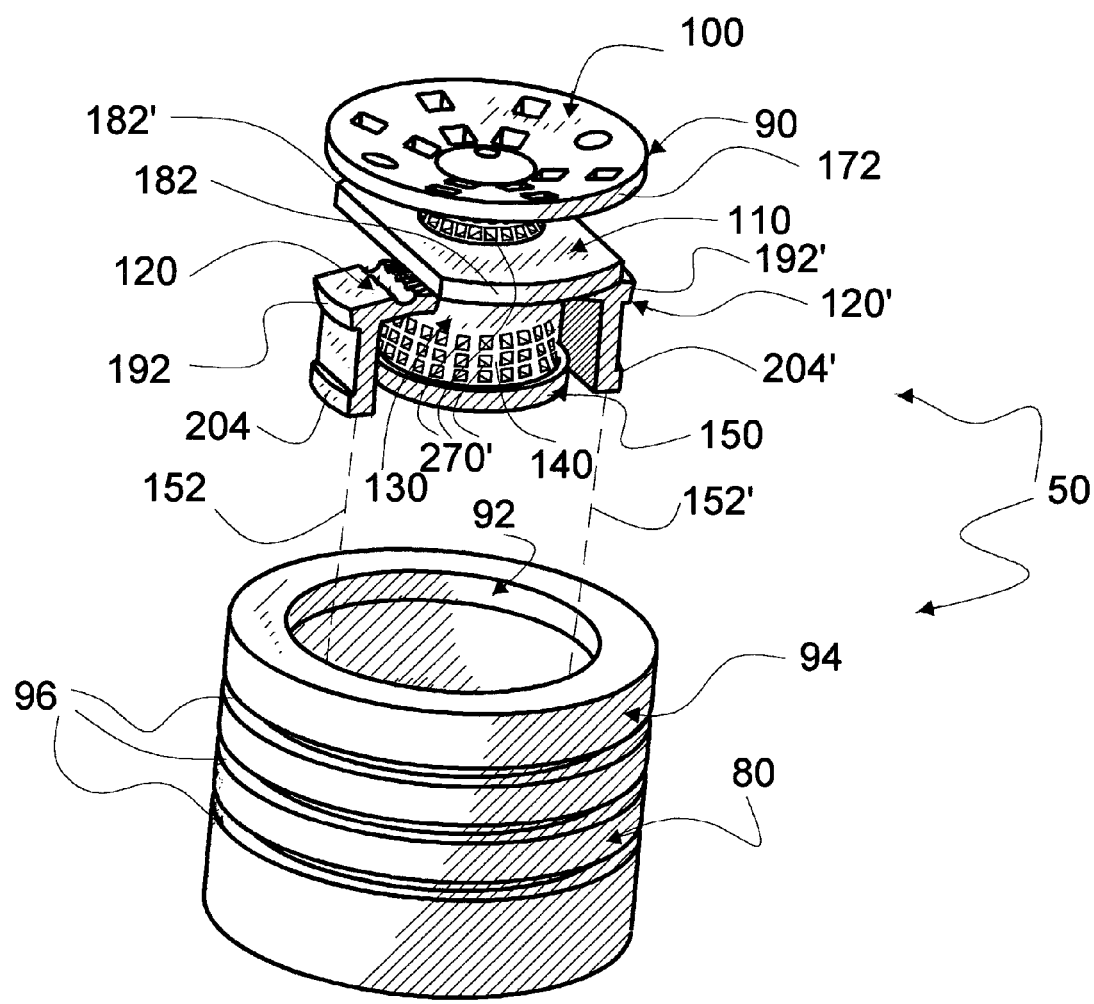
FIG. 4 is an exploded view of the valve assembly seen in FIG. 3 showing a valved stopper apart from a valve actuator.

Additional details of valved stopper 80 and valve actuator 90 are seen in FIG. 4. Valved stopper 80 has an outer cylindrical wall 94 which has pattern of annular grooves, generally numbered 96, to facilitate sealingly wiping of inner surface 46 of barrel 20 as valve assembly 50 is displaced therealong (see FIG. 2A). Within well 92, valved stopper 80 comprises a plurality of grooves disposition and purpose of which are disclosed in more detail hereafter.

Valve actuator 90 comprises a proximal stabilizing disk 100, a medially disposed stabilizing plate 110, a pair of actuator arms, 120 and 120', a medially disposed support body 130, into which is formed a gas separator vessel 140 and an annular connecting lip 150. Valve actuator 90 is displaced into well 92 as indicated by dashed lines 152 and 152'.

Figure 5:
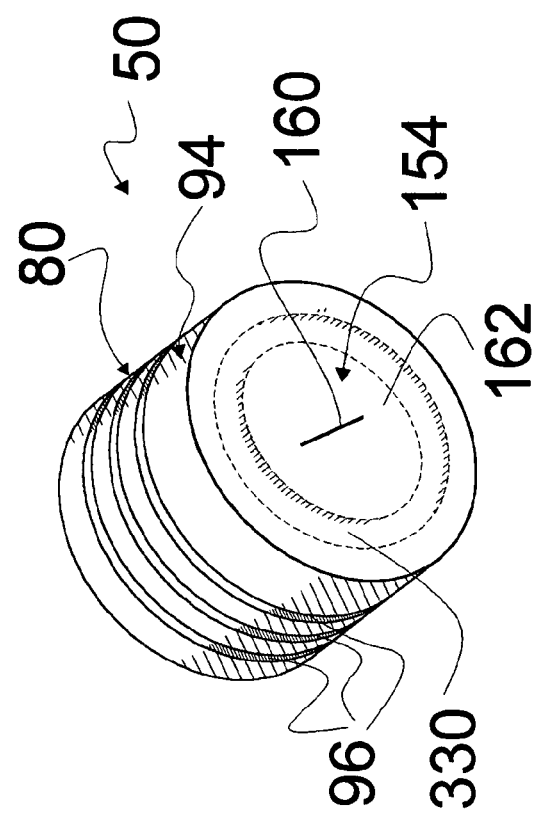
FIG. 5 is a perspective of the valved stopper rotated such that the distal side of a slit valve is seen.

Distal end 154 of valve assembly 50 is seen in FIG. 5. Note, presence of a slit 160 which is medially disposed through a distal wall 162 of valved stopper 80. Slit 160 is formed as a closed valve which remains fluid tight until selectively opened as disclosed in detail hereafter.

Figure 6:
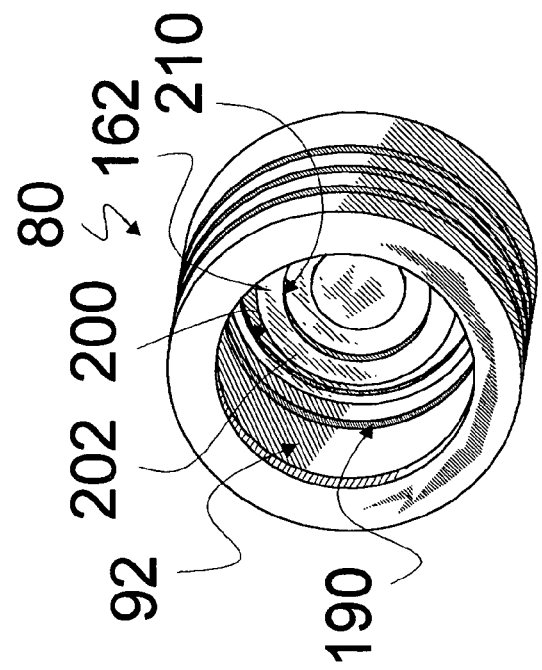
FIG. 6 is a perspective of a valved stopper, which is similar to the valved stopper seen in FIG. 5, but rotated such that the proximal side of the valve is seen.
Figure 9A:
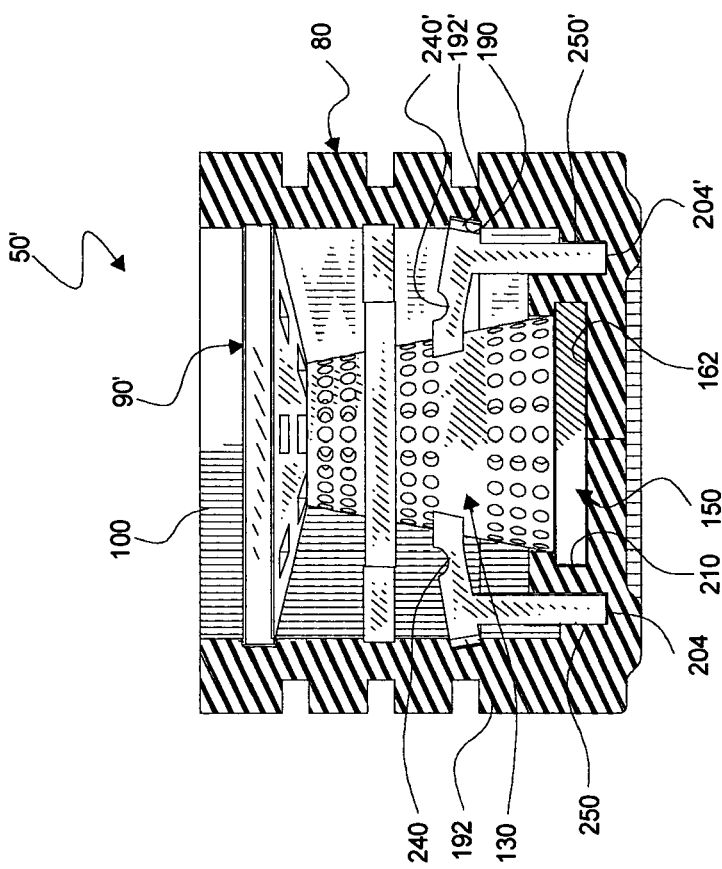
FIG. 9A is a lateral side view of a valve assembly which is similar to the assembly seen in FIG. 9, but wherein a valve assembly is differently affixed to the valved stopper.
Figure 9:
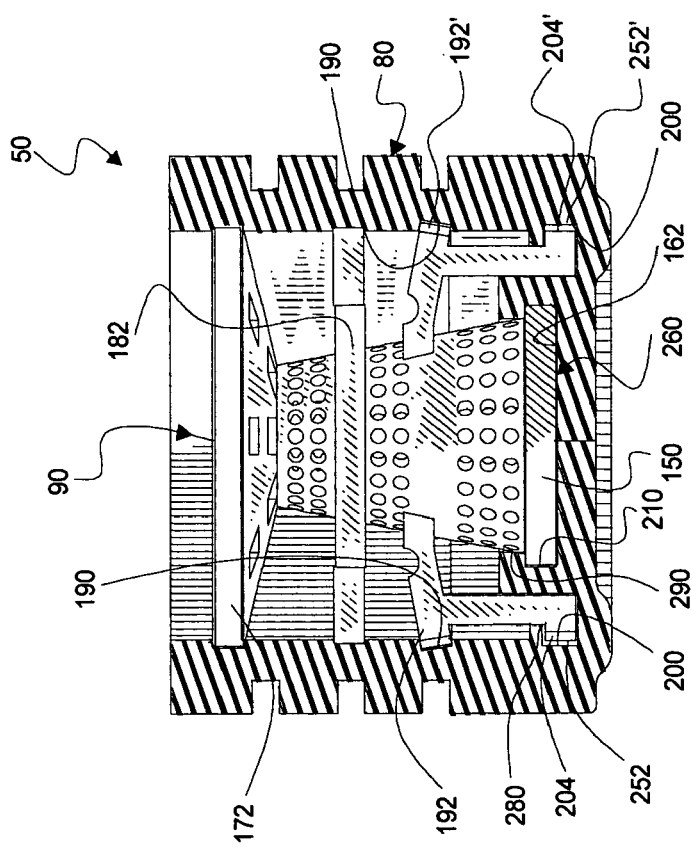
FIG. 9 is a lateral side view of a valve assembly having an actuator which is similar to the actuator seen in FIGS. 7 and 8, the actuator being disposed in a section of a valved stopper.

Greater detail of construction of well 92 is seen in FIG. 6. Valved stopper 80 has a plurality of grooves and associated slots, each of which serve a specific purpose. However, there are no grooves for rim 172 of disk 100 and outer edges 182 and 182' of plate 110. Such grooves would impede distal displacement of valve actuator 90 within valve stopper 80. Such distal displacement is necessary for valve action, as is disclosed in detail hereafter. A groove 190 coincides with protrusions 192 and 192' of arms 120 and 120' (see FIG. 4), respectively. A slot 200, disposed on the inner side 202, of distal wall 162, coincides with extremities 204 and 204' of arms 120 and 120' (again see FIG. 4). Finally, an annular slotted groove 210 is also disposed on the inner side 202 of distal wall 162 to coincide with annular connecting lip 150, also seen in FIG. 4. Greater detail concerning interfaces between valved stopper 80 and valve actuator 90 is seen in FIG. 9.

Figure 8:
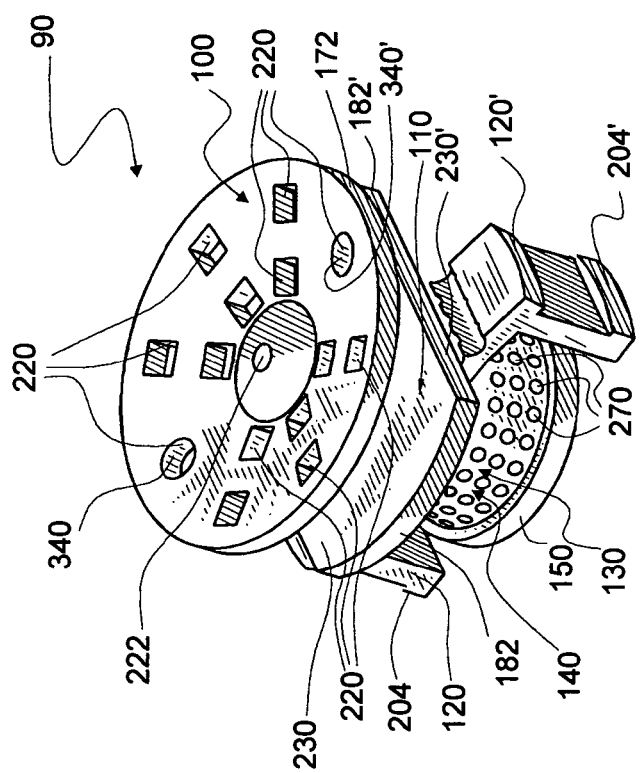
FIG. 8 is a perspective of the valve actuator, seen in FIG. 7, but rotated such that the proximal side of the actuator is seen.
Figure 7:
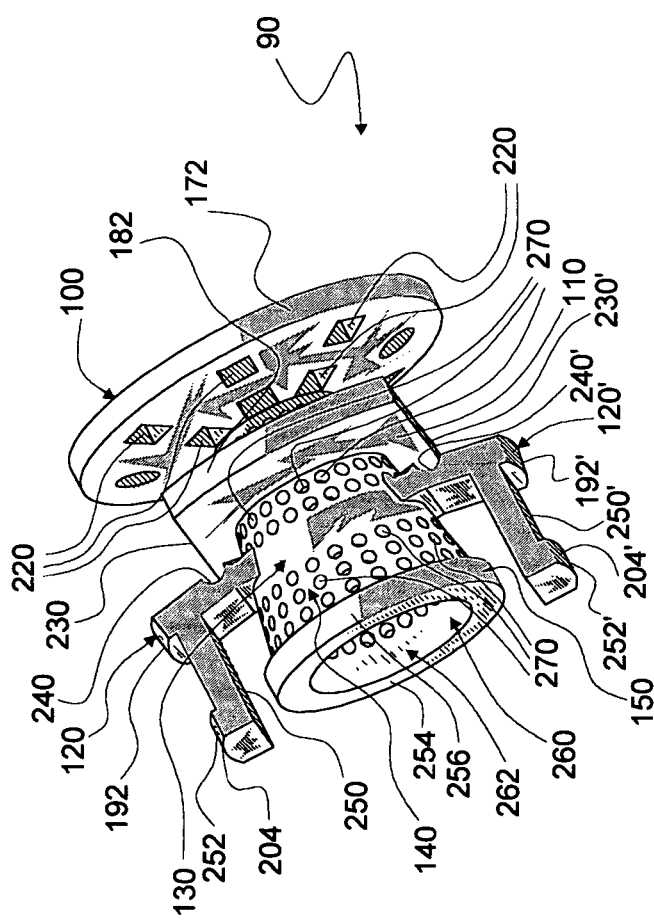
FIG. 7 is a perspective of the valve actuator, rotated such that the distal side of the actuator is seen.

Reference is now made to FIGS. 7 and 8, wherein valve actuator 90 is seen. Stabilizing disk 100 has outer rim which is disposed within well 92 (see FIG. 4) to provide a stabilizing plane for valve assembly 50. Further, disk 100 has a plurality of holes, generally numbered 220, which are sufficiently large to freely pass fluid therethrough. In addition, as seen in FIG. 8, disk 100 has a centrally disposed hole 222 which is also sufficiently large to pass all forms of fluid therethrough.

Stabilizing plate 110 has circularly formed outer edges, 180 and 182'. Edges 180 and 180' are truncated by elongated planar edges 230 and 230' to provide linear access between selected holes (disclosed in detail hereafter) between stabilizing disk 100 and arms 120 and 120', respectively. Need for such access is also disclosed hereafter.

Each actuator arm 120 and 120' is connected to body 130 through a living hinge 240 and 240', respectively (see FIG. 7). For simplicity, only actuator arm 120 is described hereafter in detail. However, it should be understood that parts associated with actuator arm 120' are simply as mirror images (with referencing numbers being primed) of parts of actuator arm 120.

Disposed radially outward from hinge 240 is protrusion 192 (again see FIG. 7), which coincides with slot 190, see FIG. 6. Transversely disposed to protrusion 192 is a limb 250, which provides an extension reaching to extremity 204. Note that extremity 204 has an outwardly disposed foot 252. Extremity 204 and foot 252 coincide with slot 200, as is better seen in FIG. 9. Note, that foot 252 is optional and may not be used as is seen in FIG. 9A.

Referring once more to FIG. 7, gas separator vessel 140 is frustoconically shaped, having a distal mouth 260 encircled by annular lip 150 and a hollow inner chamber 262. While annular lip 150 is seen to be unitary in form, a plurality of protrusions might be used. However, a single lip is preferred. Note (in FIG. 7) that lip 150 has a planar distal face 254 and an outer rim 256 which interfaces with distal wall 162 in annular slotted groove 210 of valved stopper 90 (see FIG. 6) to provide a fluid tight seal thereby.

Vessel 140 has an annular surface which is marked by a plurality of small holes, generally numbered 270. Holes 270 are sized to provide a lower resistant path for liquid into chamber 262 while imparting a much higher resistance to influent flow of gas from the outside of chamber 262 when chamber 262 is filled with liquid. Therefore, when chamber 262 is primed (filled with liquid), only liquid flows into chamber 262 from proximal chamber 60, thereby effectively separating gas from liquid from an externally disposed fluid and delivering only liquid through mouth 260.

To assure only liquid is contained within chamber 262, chamber 262 must be primed. Such priming is facilitated by filling proximal chamber 60 from an open stopper 40 end of barrel 20, barrel 20 being maintained in an upright state. Gas contained in chamber 262 is purged through hole 222, see FIG. 8. If desired, added energy may be applied to assure purging of chamber 262, such as by application of low frequency vibration or of ultrasound. Note that a holding space between stabilizing disk 100, distal wall 162 of valved stopper 80 and side walls of well 92 provides a cavity outside vessel 140 wherein undelivered gas is captured. As a caution, it should be noted that the volume of gas inside chamber 60 should not exceed the holding space.

Figure 14:
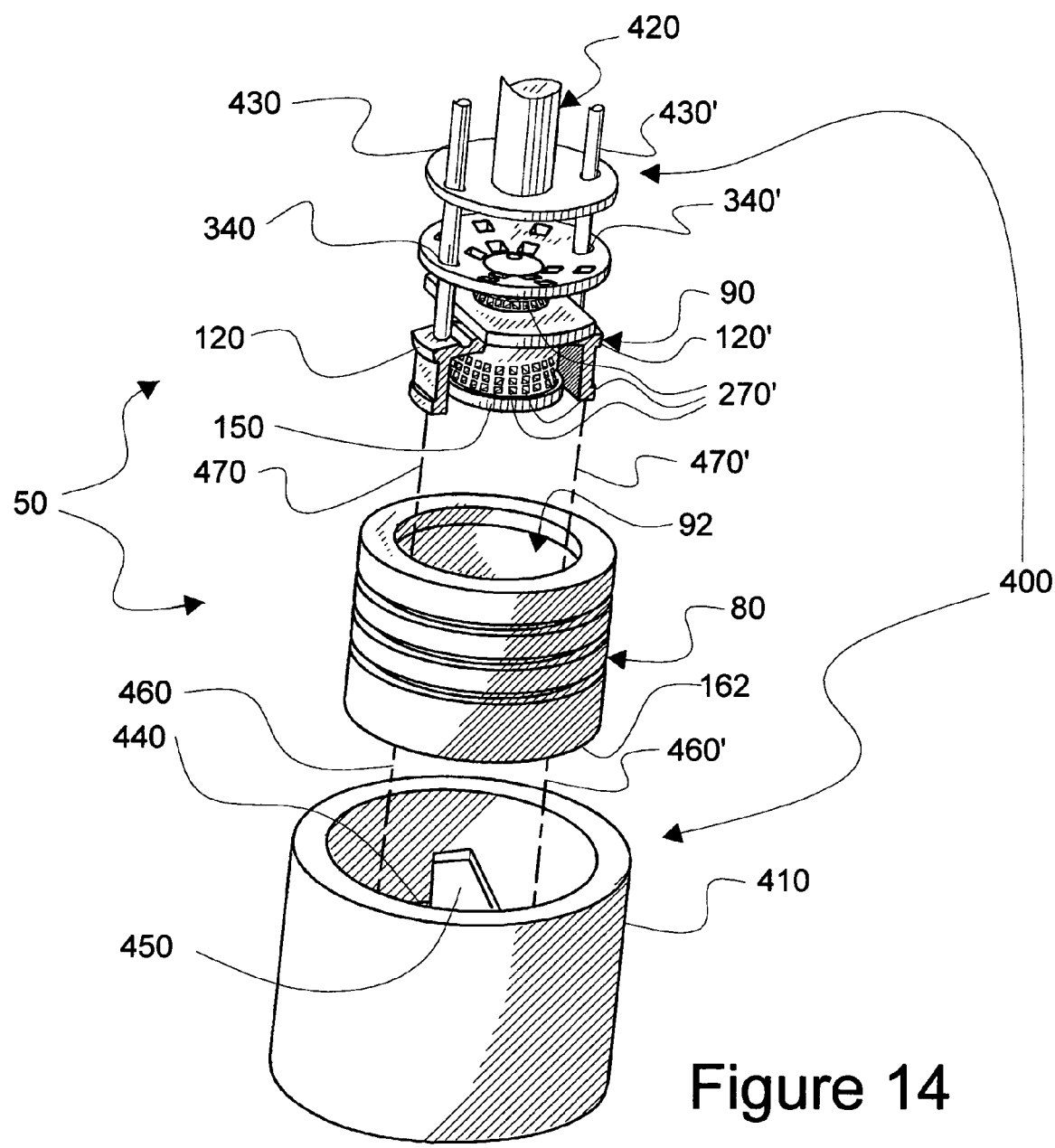
FIG. 14 is a perspective of parts of an assembly fixture and parts of a valve assembly arrayed in an assembly sequence.

Size of holes 270 is critical to vessel 140 operating as a gas separator. Examples of such hole sizes are found in commercial filters made for water sprinkler applications. As examples, a Toro product package provides such a filter in a 570 fixed spray nozzle, model number 53320. Another example is a filter available in a Rainbird National Sales Corporation, 7590 Britannia Court, San Diego, Calif. 92154 model 15EST-C1 package. The Toro and Rainbird filters are manufactured by injection molding, having holes which are usually rectangular in form and which range from 0.5 to 1.0 millimeters on a side. It may be noted that holes 270 in FIGS. 7 and 8 are seen to be round. However, rectangular holes 270', as seen in FIGS. 4 and 14, may be preferred as being easier to mold. Shape of holes (such as holes 270 and 270') is somewhat irrelevant, more important is selecting a hole size for each selected shape that properly impedes gas flow from a fluid environment.

An assembled valve assembly 50 is seen in FIG. 9, with valved stopper 80 being seen in cross section. Note correspondence of slot 190 and protrusions 192 and 192', slot 200 and extremities 204 and 204' and slot 210 and lip 150. Note, also, that slot 200 has an associated rib 280 which is inwardly disposed to catch upon feet 252 and 252' of extremities 204 and 204', respectively, securely affix extremities 204 and 204' to distal wall 162. Likewise, slot 210 has an associated inwardly disposed rib 290 which catches upon lip 150 to securely affix mouth 260 against distal wall 162. In this manner, valve actuator 90 is securely affixed to valved stopper 80 such that, when valved stopper is displaced by action of fluid and stopper 40, valve actuator 90 is likewise displaced.

A valve assembly 50' is seen in FIG. 9A. Valve assembly 50' is like valve assembly 50 except that limbs 250 and 250' terminate in extremities 204 and 204', respectively, which are devoid of feet (such as feet 252 and 252', seen in FIGS. 7 and 9. Lack of such feet requires that all displacement force upon valve actuator 90 must be derived through forces applied to lip 150 and protrusions 190 and 190'. Note that such forces may not be as effectively applied against protrusions 190 and 190' as they are connected to body 130 through living hinges 240 and 240'.

Figure 10:
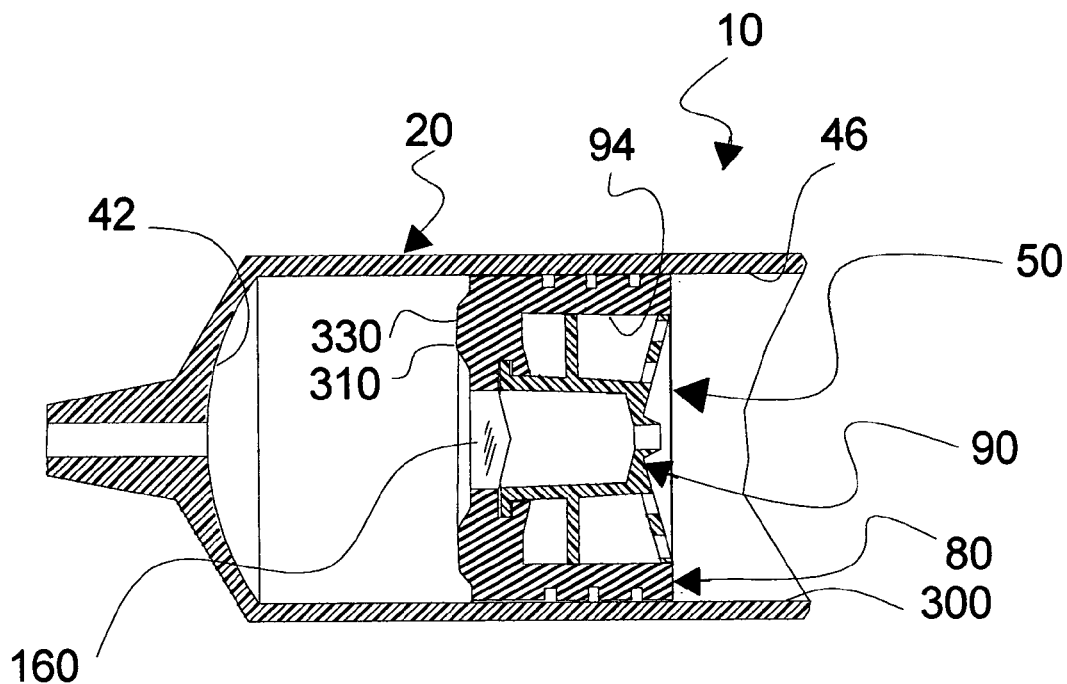
FIG. 10 is a medial section of a distal portion of a syringe barrel and a valve assembly disposed therein, the valve assembly being oriented transverse to a slit for a valve in the valved stopper portion of the valve assembly.
Figure 11:
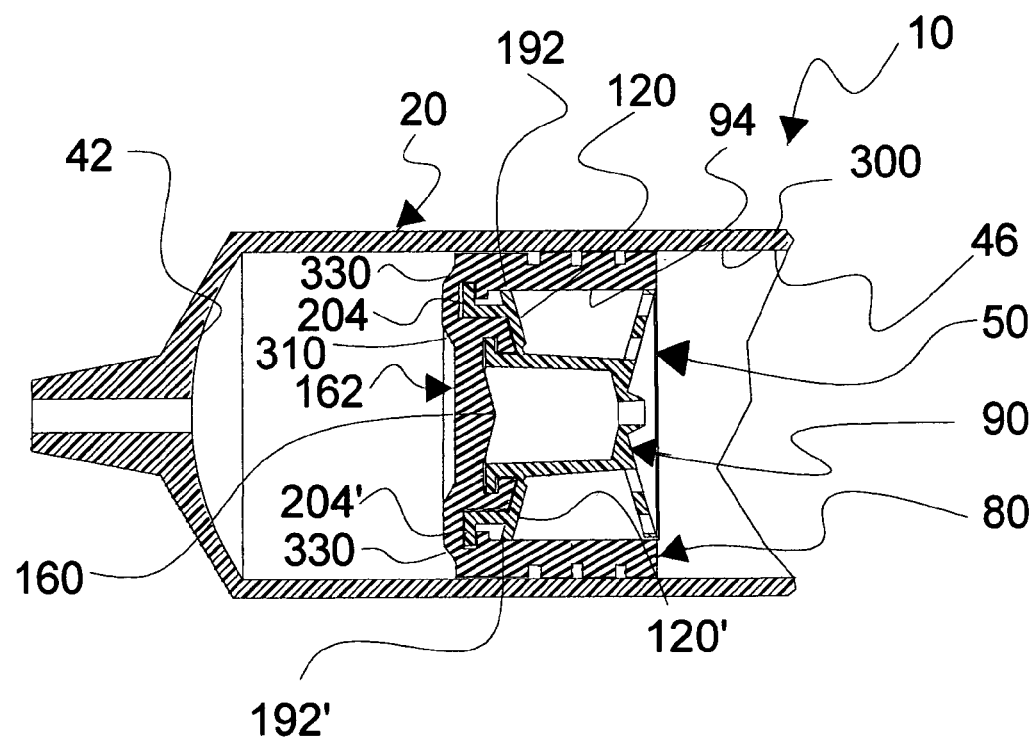
FIG. 11 is a medial section of a distal portion of a syringe barrel and a valve assembly disposed therein similar to the section seen in FIG. 10, but with the valve assembly being rotated to be oriented parallel to a slit for a valve in the valved stopper portion of the valve assembly.

Reference is now made to FIGS. 10–13 wherein valve assembly 50 is seen in two states. In the first state, valve assembly 50 is seen to be proximally displaced from distal end 42 of syringe barrel 20, as seen in FIGS. 10 and 11. Note the state of angulation of actuator arms 120 and 120', as seen in FIG. 11. Each arm (120 and 120') is angularly disposed to form an acute angle with more proximal portion 300 of inner surface 46 of syringe barrel 20. So disposed, medially directed force resulting from compression of outer cylindrical wall 94 upon protrusions 192 and 192', is placed upon slit 160 through each extremity 204 and 204'. It may be noted that no slot 190 is seen in FIGS. 10–13 as inclusion of such a slot is optional. Note also, that, as long as force is evenly distributed across distal face 310 of distal wall 162, the state of valve actuator 90 remains as seen in FIGS. 10 and 11.

Figure 13:
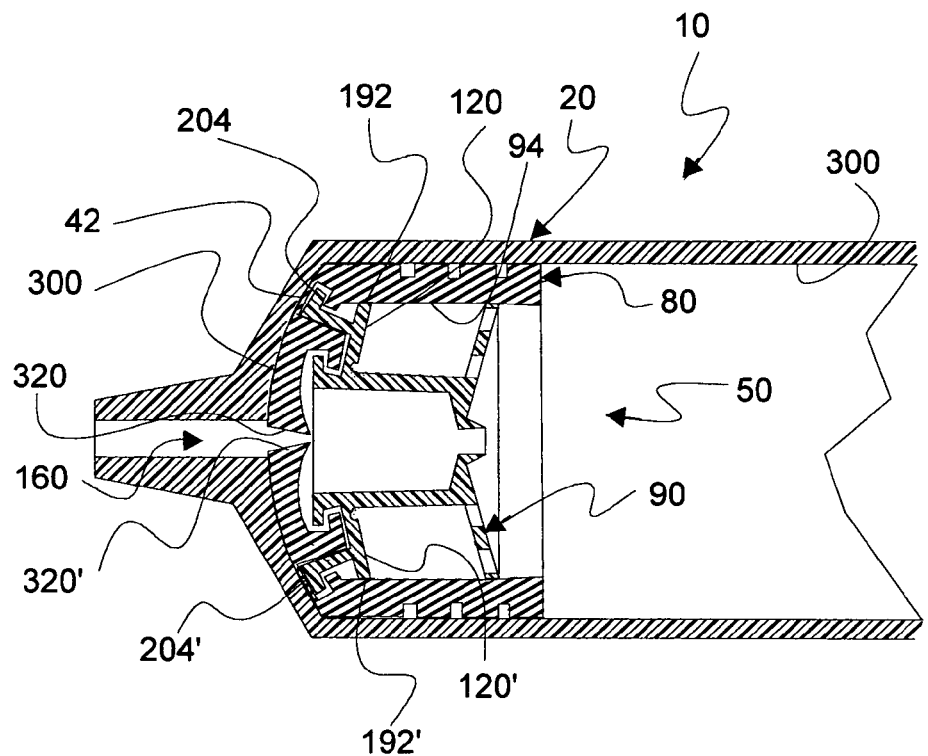
FIG. 13 is a medial section of the distal portion of syringe barrel and valve assembly seen in FIG. 12, but rotated 90 degrees such that an open valve is seen.

However, upon collision of distal face 310 against distal end 42 of syringe 20, actuator arms 120 and 120' are canted proximally as seen in FIG. 13. Protrusions 192 and 192' are resultingly forced from a first stable state (as seen in FIG. 11) through an unstable state of high compression against wall 94 to a second stable state (seen in FIG. 13). Note that compression against protrusions 192 and 192' tend to maintain an obtuse angle between the more proximal portion 300 of barrel 20 and actuator arms 120 and 120'. At this angle, protrusions 192 and 192' act as latches. Note also that articulation of arms 120 and 120' draws against slit 160, parting lips 320 and 320' of slit 160 to allow liquid flow therethrough. Note that when protrusions 192 and 192' are so latched, no additional force may be required to keep lips 320 and 320' apart.

Figure 12:
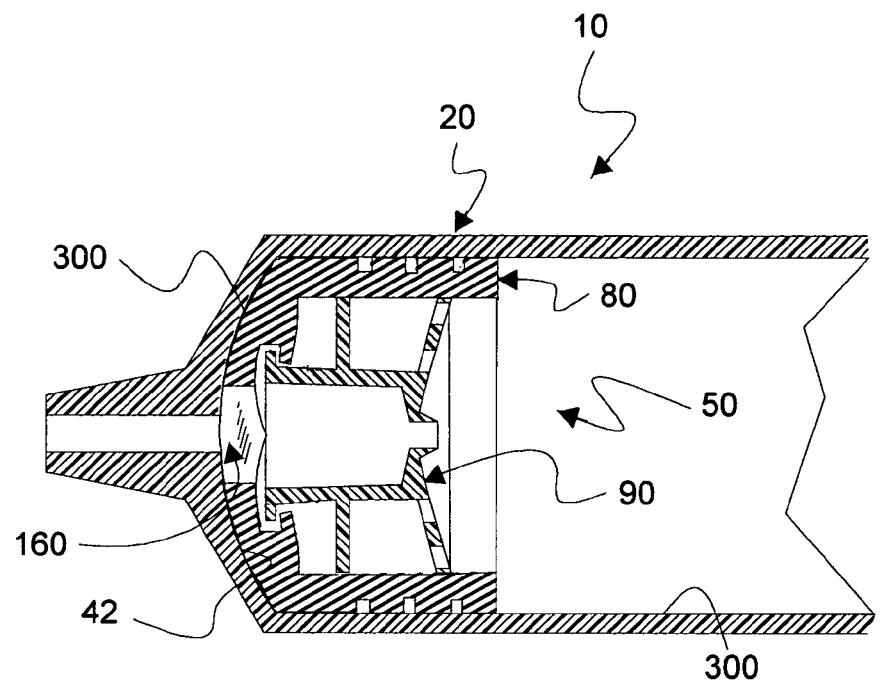
FIG. 12 is a medial section of a distal portion of a syringe barrel and a valve assembly disposed at a distal end of the syringe barrel where the slit valve is open, the valve assembly being oriented transverse to the slit of the valve in the valved stopper portion of the valve assembly.

To assure sufficient material is available to communicate displacement of extremities 204 and 204' to likewise displace lips 320 and 320' and thereby provide an open valve, an annular ring 330 which raises the surface of distal face 310 as seen in FIGS. 5, 10 and 11 may be provided. Such a raised ring, such as ring 330, may also provide an earlier point of contact where a first collision occurs between distal face 310 and distal end 42 of syringe barrel 20. Of course, material for valved stopper 80 may be either the same or similar to material generally used for syringe stoppers. However, consideration should be given to material which deforms to conform to an internal distal surface of a syringe, as seen in FIGS. 12 and 13. Should material be selected which does not seal effectively under pressure, consideration may be given to releasibly sealing slot 160 by vulcanization using applied heat or laser energy.

It may be noted, in reference to FIG. 8, that holes 220 are circular and bear the numbers 340 and 340'. Holes 340 and 340' are aligned with articulating arms 120 and 120', respectively. As is seen in FIG. 14, this alignment may be profitably used in a process of assembling valve assembly 50.

An assembly fixture 400 is seen to comprise an assembly well 410, an assembly piston and associated alignment disk 420 and a pair of alignment rods 430 and 430'. Well 410 comprises a depth limiting shelf 440 and a medially and outwardly disposed blade 450. To assemble valve assembly 50, valved stopper 80 is displaced into well along lines 460/460' as seen in FIG. 14. Alignment rods 430 and 430' are displaced through holes in assembly piston and disk 420 and therefrom through holes 340 and 340', respectively, into contact with arms 120 and 120'. Valve actuator 90 is then displaced into well 92 along lines 470/470'. Valve actuator 90 and valved stopper 80 are then further displaced into assembly well 410 until blade 450 breaches distal wall 162 to form slit 160 (not seen in FIG. 14). Valved stopper 80 is then forced against shelf 440 causing distal wall 162 to be there retained and to be deformed to accept at least installation of lip 150 into slot 210. In this manner, valve assembly 50 is assembled in one continuous motion. Transverse eying of alignment rods 430 and 430' transversely relative to blade 450 assures proper alignment of slit 160 to arms 120 and 120'.

It is important that arms 120 and 120' are distally canted to assure proper assembly into valve assembly 50. For a similar reason, installation of valve assembly into a syringe barrel, e.g. barrel 20, must also be made with assurance that arms 120 and 120' will remain so canted. For this reason, a syringe loading fixture which employs an assembly piston and disk 420 and alignment rods 430 and 430' is recommended. However, no other alignment is required when installing valve assembly 50 in a syringe barrel.

As may be seen in FIG. 15, more than one valve assembly 50 may be used in a syringe barrel 20. Placing a second valve assembly 50 distal from a first valve assembly 50 creates an intermediate chamber 60'. By forming stabilizing disk 100 to effectively match convex shape of distal end 42 of syringe 20, collision of the more proximally disposed first valve assembly will operate to open and dispense liquid 78 from chamber 60 upon collision of first valve assembly 50 with disk 100 of the second valve assembly 50. Note that liquid 78' is dispensed from chamber 60' before liquid 78 is dispensed from chamber 60. Also, any gas 76' associated with fluid 72' is trapped in the second valve assembly 50.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed and desired to be secured by Letters Patent is:

1. A multi-chamber syringe apparatus for sequentially dispensing medical fluids, said apparatus comprising:
   a syringe barrel which is concentrically disposed about an elongated medial axis, said barrel comprising an open proximal end and a distal end having a closed interior surface about an orifice through which fluid is transferred, said surface having a substantially concave shape;
   a plunger and plunger stopper combination disposed to be displaced within said barrel for dislocating fluid thereby; and
   a valve assembly disposed within said barrel between said plunger stopper and said distal end to provide a proximal chamber between the valve assembly and plunger stopper and a distal chamber between the valve assembly and said interior surface;
   said valve assembly comprising:
      a valved stopper comprising a distal face and a hollow, grooved, cylindrical interior which opens proximally toward said plunger stopper and which communicates with said plunger stopper via fluid within the barrel, therebetween, to be displaced as the plunger stopper is displaced;
      said valved stopper further comprising an operable, normally closed valve, which permits displacement of fluid therethrough only when open, and a pliable material whereby said distal face cooperatively conforms to the shape of the interior surface when forced thereupon; and
      a valve actuator comprising features which are complimentary to grooves of the interior of the valved stopper whereby the actuator is securely affixed to the valved stopper and is displaced as the valved stopper is displaced;
      said actuator further comprising structure for sensing impact between said distal face and said interior surface and, upon sensing the impact, reactively causes said valve to open.

2. Apparatus according to claim 1 wherein said actuator comprises a medially disposed elongated body which comprises a hollow opening which communicates with said valve.

3. Apparatus according to claim 2 wherein said actuator comprises at least one stabilizing element, affixed to said body which acts upon the valved stopper to resist canting of the valved stopper within the barrel to thereby assure stability of the valved stopper during forcible displacement by the plunger and plunger stopper combination.

4. Apparatus according to claim 3 wherein said at least one stabilizing element comprises a circular disk sized and shaped to provide support within the hollow of the valved stopper.

5. Apparatus according to claim 2 wherein said valve comprises a slit disposed through the distal face of said valved stopper.

6. Apparatus according to claim 5 wherein said stopper comprises a size and shape relative to said hollow syringe barrel which maintains said slit in a normally closed state unless acted upon by a valve opening mechanism of said impact sensing structure.

7. Apparatus according to claim 5 wherein said impact sensing structure comprises an arm which comprises a hinged connection to said body, said arm having a distally extending appendage which communicates with said inner surface through said distal face upon impact between the distal face and inner surface articulates to open said slit.

8. Apparatus according to claim 7 wherein said arm further comprises an outwardly extending part which is in contact with the hollow cylindrical interior of said stopper and which articulates as said arm articulates.

9. Apparatus according to claim 8 wherein said arm and said part couple comprise sufficient length away from said hinged connection to compressively act to forcibly maintain said slit closed prior to impact between said closed face and the inner surface.

10. Apparatus according to claim 8 wherein said part comprises sufficient length to be securely but releasibly affixed by the cylindrical interior of the stopper when angularly distally disposed toward said distal face to provide a latch for maintaining said valve closed prior to articulation of said arm and part.

11. Apparatus according to claim 8 wherein said part comprises a length which permits forcible articulation of said part from being angularly distally disposed to be angularly proximally disposed as said arm and part are articulated upon impact.

12. Apparatus according to claim 8 wherein said part comprises sufficient length to be retained by the cylindrical interior of the stopper in a proximally angularly disposed state relative to said distal face to thereby provide a latch for maintaining said valve open following articulation of said arm and part.

13. Apparatus according to claim 2 wherein said valve actuator body further comprises a gas separator interposed between said proximal chamber and said valve.

14. Apparatus according to claim 13 wherein said gas separator comprises a hollow body having a distal mouth having an orifice which opens about said valve and which otherwise impedes fluid flow through said valve.

15. Apparatus according to claim 14 wherein said valve actuator body comprises an elongated shape, thereby providing a support for said at least one stabilizing element and the impact sensing structure.

16. Apparatus according to claim 14 wherein said body of said gas separator comprises a plurality of holes of predetermined size which pass liquid in preference to gas when said body is primed with liquid.

17. Apparatus according to claim 14 wherein said valve actuator body comprises a frustoconical shape.

18. Apparatus according to claim 14 wherein said valve actuator body comprises a proximal hole medially disposed therein, said proximal hole having sufficient diameter to permit air to be purged therethrough for the purpose of priming said body with liquid.

19. A combination for providing a sequentially dispensing, multi-chamber syringe, said combination comprising:
   a hollow syringe barrel having a distal end which is closed except for a fluid transfer orifice;
   a syringe plunger;
   a valve assembly distally disposed in the syringe barrel relative to the syringe plunger, the valve actuator separating space within the barrel into proximal and distal chambers;
   said valve assembly comprising:
      a valved stopper comprising a stopper body comprising a normally closed valve element; and
      a valve actuator rigidly affixed to said valved stopper, said valve actuator comprising at least one stabilizing element for stabilizing said valved stopper within the barrel, a sensor arm which senses impact between the valved stopper and the closed distal end of the syringe barrel and which articulates upon such impact to open the valve element, a gas separator which separates gas from liquid flowing from the proximal chamber thereby permitting only liquid to be dispensed thereby.

20. A method for assembling a valve actuator for use in dividing a syringe into proximal and distal chambers, to thereby provide a sequential delivery multi-chamber syringe apparatus, comprising the steps of:

providing a valve actuator having at least one distally disposed connecting lip:

providing a stopper having a hollow cylindrical body having an annular side for compressibly interfacing with an interior surface of a hollow syringe barrel and a closed, substantially circular surface at one end of the side, said stopper further comprising at least one grooved slot whereby said at least one lip, and, therefore, said valve actuator are securely affixed to said stopper;

providing an assembly fixture having an open annular well with an internal ledge sized and shaped to receive and support the stopper when disposed thereat, said fixture further comprising a blade having a sharpened tip medially and transversely disposed relative to said ledge, said sharpened tip being directed outward from the open well;

displacing the stopper into said fixture such that the closed surface opposes the sharpened tip; and displacing the valve actuator into the hollow body of the stopper, thereby forcing the at least one lip to be securely affixed to the at least one grooved slot thereby engaging and securing the actuator to the stopper and simultaneously forcing the sharpened tip through the closed circular surface to form a slit for a slit valve thereby.

21. A method for using a valve assembly as a chamber divider in a multi-chamber, sequentially dispensing syringe comprising the steps of:

providing a syringe having a syringe barrel which is concentrically disposed about an elongated medial axis, said barrel comprising an open proximal end and a distal end having a closed interior surface about an orifice through which fluid is transferred, said surface having a substantially concave shape;

providing a plunger and plunger stopper combination, associated with the syringe, disposed to be displaced within said barrel for dislocating fluid thereby; and providing a valve assembly disposed within said barrel between said plunger stopper and said distal end to provide a proximal chamber between the valve assembly and plunger stopper and a distal chamber between the valve assembly and said interior surface;

said valve assembly comprising:

a valved stopper comprising a distal face and a hollow, grooved, cylindrical interior which opens proximally toward said plunger stopper and which communicates with said plunger stopper via fluid within the barrel, therebetween, to be displaced as the plunger stopper is displaced;

said valved stopper further comprising an operable, normally closed valve, which permits displacement of fluid therethrough only when open, and a pliable material whereby said distal face cooperatively conforms to the shape of the interior surface when forced thereupon; and a valve actuator comprising features which are complimentary to grooves of the interior of the valved stopper whereby the actuator is securely affixed to the valved stopper and is displaced as the valved stopper is displaced;

said actuator further comprising structure for sensing impact between said distal face and said interior surface and, upon sensing the impact, reactively causes said valve to open;

installing said valve assembly at a predetermined site in the barrel of the syringe;

filling the proximal chamber with a predetermined first liquid;

inserting the plunger and plunger stopper combination to seal and retain the first liquid in the proximal chamber;

filling the distal chamber with a second liquid; and distally displacing the plunger and plunger stopper to sequential dispense first the second liquid from the distal chamber and then, afterward, to dispense the first liquid from the proximal chamber.

22. The method according to claim 21 wherein the dispensing step comprises distorting the valved stopper at the end of second liquid dispensing step to reduce dead space wherein a volume of the second liquid would be retained in the syringe.

23. The method according to claim 21 wherein impact of the valved stopper with the closed interior surface results in opening the valve.

24. The method according to claim 21 wherein the first liquid dispensing step further comprises separating gas from the second liquid and trapping that gas within a portion of the proximal chamber where the gas is retained and not dispensed with the first liquid.

25. The method according to claim 21 wherein the valve assembly installing and proximal chamber filling steps are repeated to form an intermediate chamber which results in providing a three chamber multi-chamber sequential delivery syringe.

26. The method according to claim 21 wherein the valve assembly installing and proximal chamber filling steps are performed more than once to form at least one intermediate chamber which is further used for delivering a sequential series of doses from the syringe.

27. A gas separator apparatus for a patient liquid delivery line, said separator apparatus comprising:

a smaller vessel having an effluent opening toward the delivery line;

a larger vessel which contains the smaller vessel, said larger vessel containing fluid which comprises a deliverable liquid outside the smaller vessel;

said smaller vessel being primed with the deliverable liquid and further comprising a series of holes which are sized to pass liquid at a lower resistance than passing gas into through the holes into the primed chamber;

said larger vessel comprising a space outside the smaller vessel wherein the gas is trapped.

* * * * *